United States Patent
Kapre et al.

(10) Patent No.: US 9,878,029 B2
(45) Date of Patent: Jan. 30, 2018

(54) PROCESS FOR PREPARATION OF POLYSACCHARIDES

(75) Inventors: Subhash Kapre, Pune (IN); Swapan Kumar Jana, Pune (IN); Tushar Dnyaneshwar Joglekar, Pune (IN)

(73) Assignee: Serum Institute of India Private Limited, Pune (IN)

( * ) Notice: Subject to any disclaimer, the term of this patent is extended or adjusted under 35 U.S.C. 154(b) by 0 days.

(21) Appl. No.: 14/006,404

(22) PCT Filed: May 9, 2011

(86) PCT No.: PCT/IN2011/000323
§ 371 (c)(1),
(2), (4) Date: Sep. 20, 2013

(87) PCT Pub. No.: WO2012/127485
PCT Pub. Date: Sep. 27, 2012

(65) Prior Publication Data
US 2014/0011265 A1    Jan. 9, 2014

(30) Foreign Application Priority Data
Mar. 22, 2011   (IN) .......................... 838/MUM/2011

(51) Int. Cl.
| | | |
|---|---|---|
| *A61K 39/09* | (2006.01) | |
| *B01D 15/32* | (2006.01) | |
| *B01D 15/36* | (2006.01) | |
| *C08B 37/00* | (2006.01) | |
| *C12N 1/06* | (2006.01) | |
| *C12P 19/04* | (2006.01) | |

(52) U.S. Cl.
CPC .......... *A61K 39/092* (2013.01); *B01D 15/327* (2013.01); *B01D 15/361* (2013.01); *B01D 15/362* (2013.01); *B01D 15/363* (2013.01); *C08B 37/0003* (2013.01); *C12N 1/06* (2013.01); *C12P 19/04* (2013.01)

(58) Field of Classification Search
None
See application file for complete search history.

(56) References Cited

U.S. PATENT DOCUMENTS

| | | |
|---|---|---|
| 4,242,501 A | 12/1980 | Cano et al. |
| 4,902,616 A | 2/1990 | Fournier et al. |
| 5,623,057 A | 4/1997 | Marburg et al. |
| 5,714,354 A | 2/1998 | Arnold et al. |
| 5,847,112 A | 12/1998 | Kniskern et al. |
| 6,248,570 B1 | 6/2001 | Michol et al. |
| 2007/0231876 A1 | 10/2007 | Biemans et al. |
| 2008/0286838 A1* | 11/2008 | Yuan et al. ................... 435/101 |
| 2010/0129881 A1 | 5/2010 | Kapre et al. |

FOREIGN PATENT DOCUMENTS

IN   1572/MUM/2010   8/2013

OTHER PUBLICATIONS

[1] GE Healthcare, "Hydrophobic Interaction and Reversed Phase Chromatography"; GE Healthcare Bio-Sciences AB: Uppsala, Sweden, 2006; Chapters 1-3, pp. 9-68.*
[2] GE Healthcare, "Ion Exchange Chromatography & Chromatofocusing"; GE Healthcare Bio-Sciences AB: Uppsala, Sweden, 2010; Chapter 2, pp. 26-54.*
Poxton, et al., The Structure of C-Polysaccharide from the Walls of *Streptococcus pneumonia*. Biochem. J., 1978, 175(3):1033-1042.
Small, et al., Strain Variation in Composition and Molecular Size of the Capsular Polysaccharide of *Cryptococcus neoformans* Serotype A. Infect. Immun., 1986, 54(3):735-741.
International Preliminary Report on Patentability issued in PCT/IN11/00323 dated Sep. 24, 2013.
International Search Report issued in PCT/IN11/00323 dated Nov. 19, 2011.
Written Opinion of the International Searching Authority issued in PCT/IN11/00323 dated Nov. 19, 2011.
Informal Comments submitted in PCT/IN11/00323 dated Oct. 4, 2013.
Section A.3.1.6.2 of Recommendations to assure the quality, safety and efficacy of pneumococcal conjugate vaccines—proposed replacement of TRS 927, Annex 2, Expert Committee on Biological Standardization, Geneva, Oct. 19-23, 2009.

* cited by examiner

*Primary Examiner* — Michelle F Paguio Frising
(74) *Attorney, Agent, or Firm* — McCarter & English, LLP; Jill Ann Mello (57) ABSTRACT

A novel alcohol and CTAB free process for purification of capsular polysaccharides, wherein the C-polysaccharide, protein, nucleic acid content of the purified polysaccharide is substantially reduced The said process is cost efficient and less laborious.

14 Claims, 13 Drawing Sheets

PROCESS FOR PREPARATION OF POLYSACCHARIDES

RELATED APPLICATIONS

This application is a 35 U.S.C. § 371 national stage filing of International Application No. PCT/IN2011/000323, filed May 9, 2011, which claims priority to Indian Patent Application No. 838/MUM/2011, filed Mar. 22, 2011. The entire contents of the foregoing applications are hereby incorporated by reference.

BACKGROUND OF THE INVENTION

The pathogenic bacteria classified as *Streptococcus pneumoniae* (pneumococci, Pn) have been subdivided into 84 antigenic serotypes, based on the capsular polysaccharide (PnPs) of the organism. Disease states attributable to these organisms include pneumonia, meningitis, otitis media, bacteremia and acute exacerbations of chronic bronchitis, sinusitis, arthritis, and conjunctivitis. The preponderance of these diseases, however, are caused by a limited subset of the 84 known isolates. Thus, a polyvalent vaccine containing the PnPs from the most prevalent and pathogenic isolates of the organism can provide protection against a very high percentage of the most frequently reported pathogens of this class.

The PnPs utilized for preparing conjugate vaccines are always associated with a substantial amount of a common impurity/contaminant, called C-Polysaccharide (C-Ps). Although the presence of the C-polysaccharide contaminant does not interfere with the immune responses against the type specific antigens, production of anti-C-polysaccharide antibodies may correlate with the tissue destruction observed in some unresolved pneumococcal infections. The C-Ps content could compromise the efficacy of a pneumococcal conjugate vaccine.

The C-Ps has also been classified as a polysaccharide impurity by WHO, refer WHO TRS 19-23 Oct. 2009 (Recommendations to assure the quality, safety and efficacy of pneumococcal conjugate vaccines).

Thus a need for improving purity of the polysaccharides i.e. reduction in contamination with group-specific C-polysaccharide always exist in the industry.

U.S. Pat. No. 4,242,501 claims ammonium sulphate based polysaccharide precipitation, wherein C-Polysaccharide content is reduced to less than 0.5%. The purification process however consists of 12 steps and utilizes alcohol for precipitation also.

U.S. Pat. No. 5,623,057 claims C-polysaccharide content less than 3% by utilizing Isopropyl alcohol based PnPs purification and also employs ion exchange chromatography before or after partial hydrolysis (Sonic or thermal) of polysaccharide.

U.S. Pat. No. 5,714,354 claims an "alcohol free" PnPs purification process, utilizes CTAB (1-4%), hydroxyapatite chromatography and ion exchange chromatography. Here CTAB step removes majority of C-polysaccharide.

U.S. Pat. No. 5,847,112 claims C-Ps reduction by 3-20 fold, However here PnPs purification comprises of multiple isopropyl alcohol and cetavlon steps.

1572/MUM/2010 claims deoxycholate & Hydrophobic interaction chromatography based (i.e. alcohol and CTAB free) purification. Here C-Ps content is 4-14%.

The prior art methods utilize CTAB, alcohol and are multi-step. CTAB has been previously utilized for selectively precipitation of polysaccharide, however CTAB is a hazardous chemical.

Further removal of CTAB from precipitated PnPs requires ethanol. Use of ethanol during pneumococcal polysaccharide purification is associated with following operational problems: a) Use of ethanol requires a flame proof facility; b) designing such facility is very costly, c) ethanol is under custom/Govt. Regulation, d) ethanol is hazardous, e) effluent treatment is very difficult f) amount of ethanol requirement is huge and it's is almost ~4-6 L of ethanol per liter of process material and g) requires costly charcoal filtration and lyophilization steps.

The prior art methods that utilize ethanol and CTAB steps require 77-90 hrs to achieve the C-Ps-reduced polysaccharide preparation and hence are laborious.

Surprisingly we have found that when a preferred single or multiple step chromatography is utilized for preparation of pneumococcal polysaccharides, a substantial reduction of group specific C-Ps content is observed. The said process being alcohol and CTAB free is easily scalable, cost efficient and less laborious.

SUMMARY OF THE INVENTION

The invention is an alcohol and CTAB free method for the purification of pneumococcal polysaccharides which are used in the preparation of polysaccharide vaccines. The instant process utilizes chromatographic separation of C-Ps from the polysaccharides (PnPs) on the basis of differences in their net surface charge. The process is a generic process to purify pneumococcal polysaccharides.

PnPs prepared by the instant process shows recovery of about 60 to 70%, wherein C-polysaccharide contamination reduction is of 1 to 5 fold as compared to the C-Ps content of post-Hydrophobic interaction chromatography (HIC) or pre ion exchange chromatography (IEX), protein contamination is less than 1% and nucleic acid contamination is less than 1%. The said process has been carried out at Research, Pilot and commercial scale.

This process can purify polysaccharides with 80-90% less time consumed & 90% less cost when compared with CTAB/Alcohol based methods.

DESCRIPTION OF THE DRAWINGS

Figures for HIC Followed by Ion Exchange Chromatography

Figures for Direct Ion Exchange Chromatography

Figures for Ion Exchange Chromatography Followed by HIC

DETAILED DESCRIPTION OF THE INVENTION

Definitions

The terms "impurity" and "contaminant", and grammatical variations thereof, are used interchangeably to mean C-polysaccharide.

The term "target polysaccharide" is used to refer to a pneumococcal capsular polysaccharide, as described above.

The term "chromatography" refers to the process by which a solute of interest, e.g., a polysaccharide of interest, in a mixture is separated from other solutes in the mixture by percolation of the mixture through an adsorbent, which adsorbs or retains a solute more or less strongly due to properties of the solute.

The term "hydrophobic interaction chromatography" refers to a method of separating a target based on the strength of its relative hydrophobic interactions with a hydrophobic separation matrix. In this context, "hydrophobicity" is defined as the repulsion between a non-polar compound and a polar environment.

The terms "ion-exchange" and "ion-exchange chromatography" refer to a chromatographic process in which an ionizable solute of interest interacts with an oppositely charged ligand linked to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

The Pneumococcal polysaccharide purification process of the instant invention comprises following steps:

(a) lysing bacterial cells with a detergent in a fermentation medium containing a *S. pneumococcal* bacterium thereby producing a lysate containing a polysaccharide solution and solid cell debri;

(b) clarifying the aqueous cell lysate by separating solids from the polysaccharide solution;

(c) concentrating the polysaccharide solution by ultrafiltration using a 100K molecular weight cutoff membrane to remove low molecular weight contaminants to form a solution of concentrated polysaccharide;

(d) treatment of the solution comprising polysaccharide with a nuclease;

(e) precipitation of impurities using ammonium sulphate or DOC-NaCl treatment;

(f) diafiltration using 100K molecular weight cutoff membrane (g) subjecting polysaccharide solution to single or multi step chromatography;

(h) concentration and diafiltration; and (i) sterile filtration of the polysaccharide solution.

According to the instant invention, Ion exchange separates Ps and C-Ps on the basis of differences in their net surface charge. Molecules vary considerably in their charge properties and will exhibit different degrees of interaction with charged chromatography media according to differences in their overall charge, charge density and surface charge distribution.

According to the instant invention the said single or multiple step chromatography can comprise of i) Hydrophobic interaction chromatography followed by ion exchange or ii) Direct Ion exchange or iii) Ion exchange followed by HIC.

Preferably hydrophobic adsorbent can be selected from but not limited to butyl-, phenyl-, and octyl-agarose and butyl-, phenyl- and ether-organic polymer resin. Capsular polysaccharide will come out as flowthrough during loading on to column and wash after loading at high-salt (2 M to 5 M or 50% saturation of ammonium salt), while the more hydrophobic protein and nucleic acids will be retained.

Further said second chromatography column is an ion exchange chromatography that can be selected from cation exchange, anion exchange, and mixed mode chromatographies.

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, Poros PI 20, PI 50, HQ 10, HQ 20, HQ 50, D 50 from Applied Biosystems, Sartobind Q from Sartorius, MonoQ, Capto Q, Eshmino Q, Gigacap Q 650M, Nuvia-Q, Cellufine Q-h, MiniQ, Source 15Q and 30Q, Q, DEAE and ANX Sepharose Fast Flow, Q Sepharose high Performance, QAE SEPHADEX™ and FAST Q SEPHAROSE™ (GE Healthcare), WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and Q800, from Millipore, Fractogel EMD TMAE, Fractogel EMD DEAE and Fractogel EMD DMAE from EMD, Amberlite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

Another embodiment of the instant invention is that said anion exchange column is eluted at 10%, 15%, 20%, 25%, 30%, 45% and 60% of 1M NaCl in phosphate buffer depending on serotypes.

Yet another aspect of the invention is that the said anion exchange column is eluted at linear or step gradient of 1M NaCl in phosphate buffer depending on serotypes, particularly the anion exchange column is eluted at: a) 10%, 15%, 20%, 25% and 30% of 1M NaCl in phosphate buffer for serotype 1; b) 10%, 15%, 20% and 45% of 1M NaCl in phosphate buffer for serotype 5; c) 20% and 35% of 1M NaCl in phosphate buffer for serotype 6B, 6A, 19A and 19F; d) 15%, 20% and 30% of 1M NaCl in phosphate buffer for serotype 23F; e) 10%, 15% and 30% of 1M NaCl in phosphate buffer for serotype 9V and f) flowthrough and 100% of 1M NaCl in phosphate buffer for serotypes 7F, 14 and 33F respectively.

Figure 1:
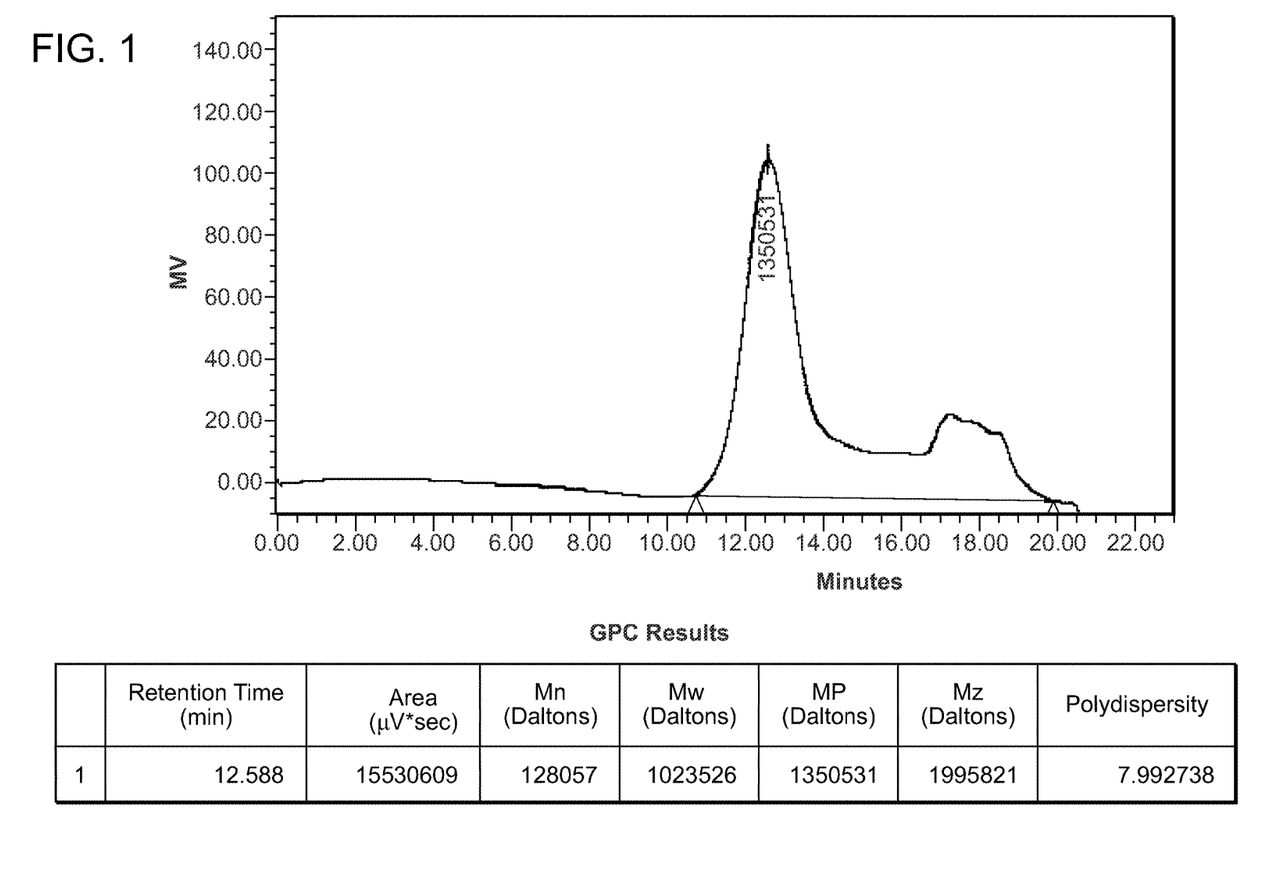
FIG. 1 Pneumococcal polysaccharide 19F-HPLC profile of pre-HIC
Figure 2:
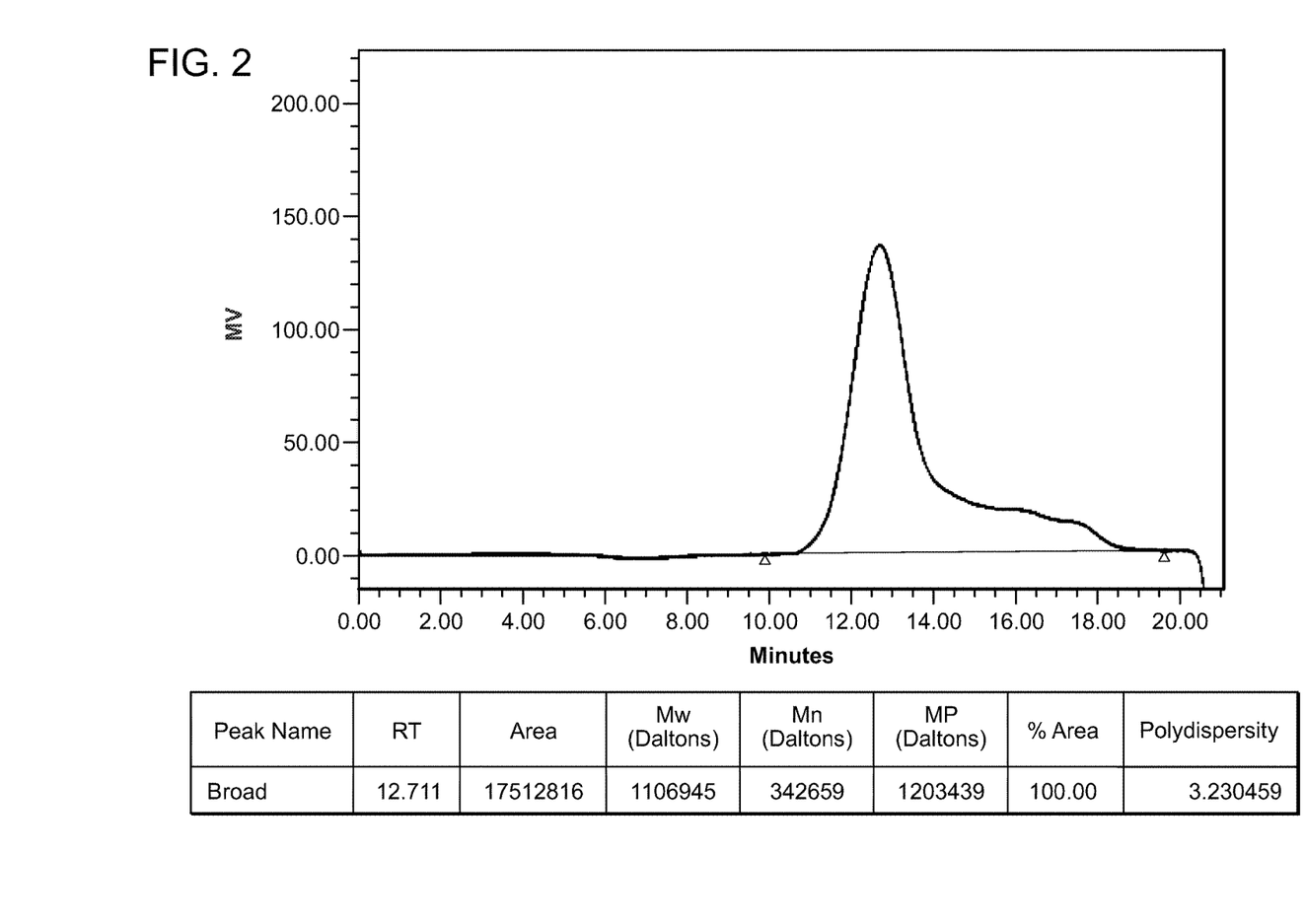
FIG. 2 Pneumococcal polysaccharide 19F-HPLC profile of post Hydrophobic Interaction Chromatography (HIC)
Figure 3:
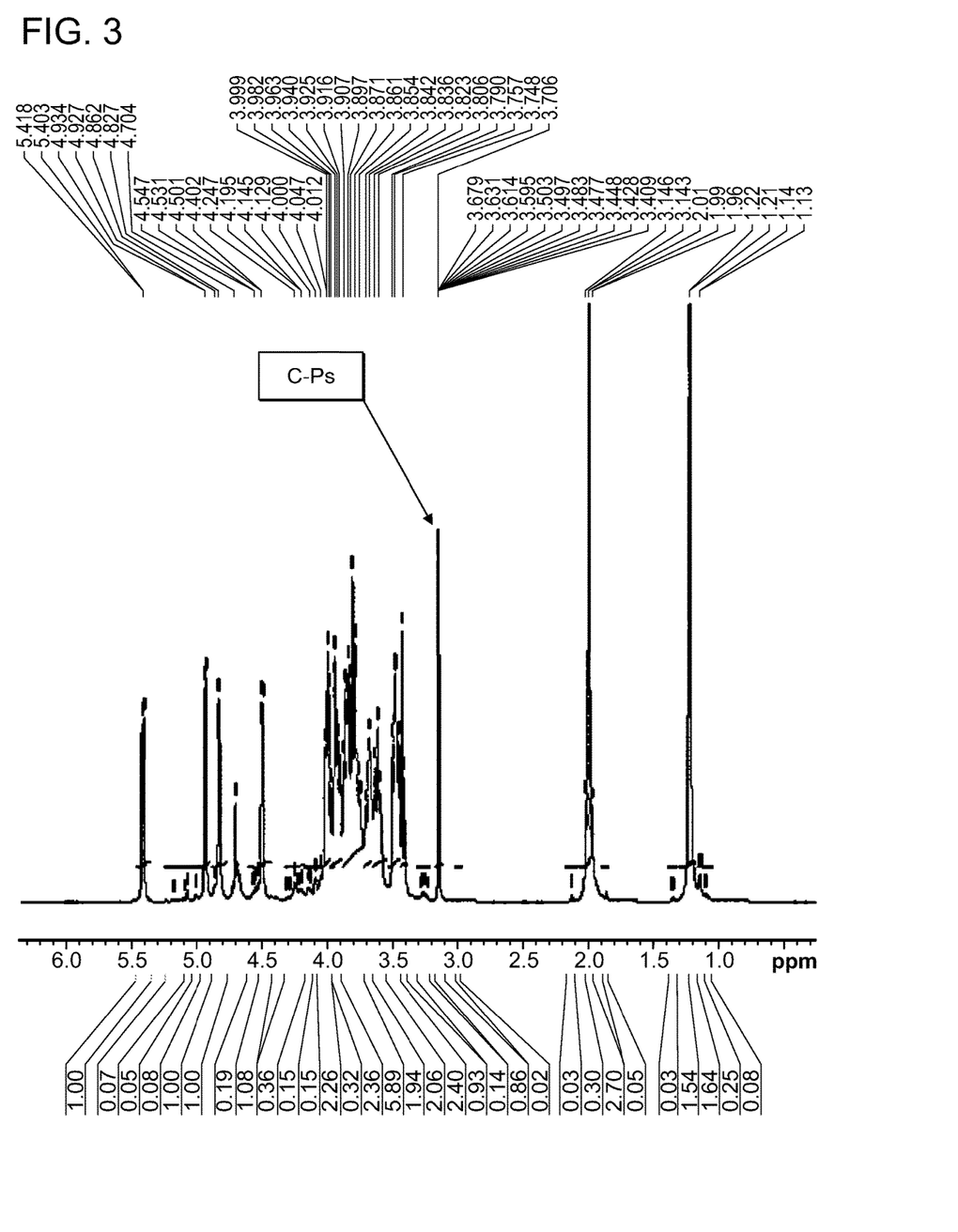
FIG. 3 NMR of 19F PnPs-post-HIC chromatography
Figure 4:
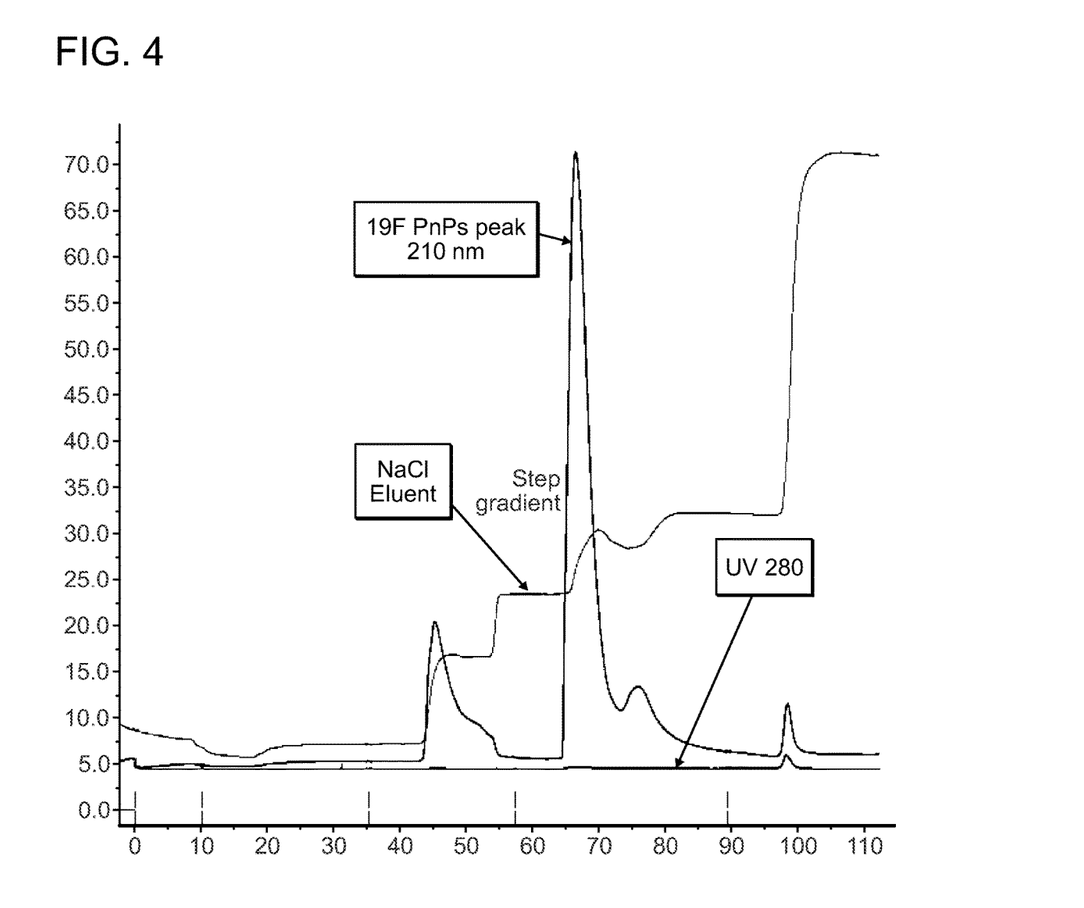
FIG. 4 Ion exchange chromatogram of HIC-purified PnPs
Figure 5:
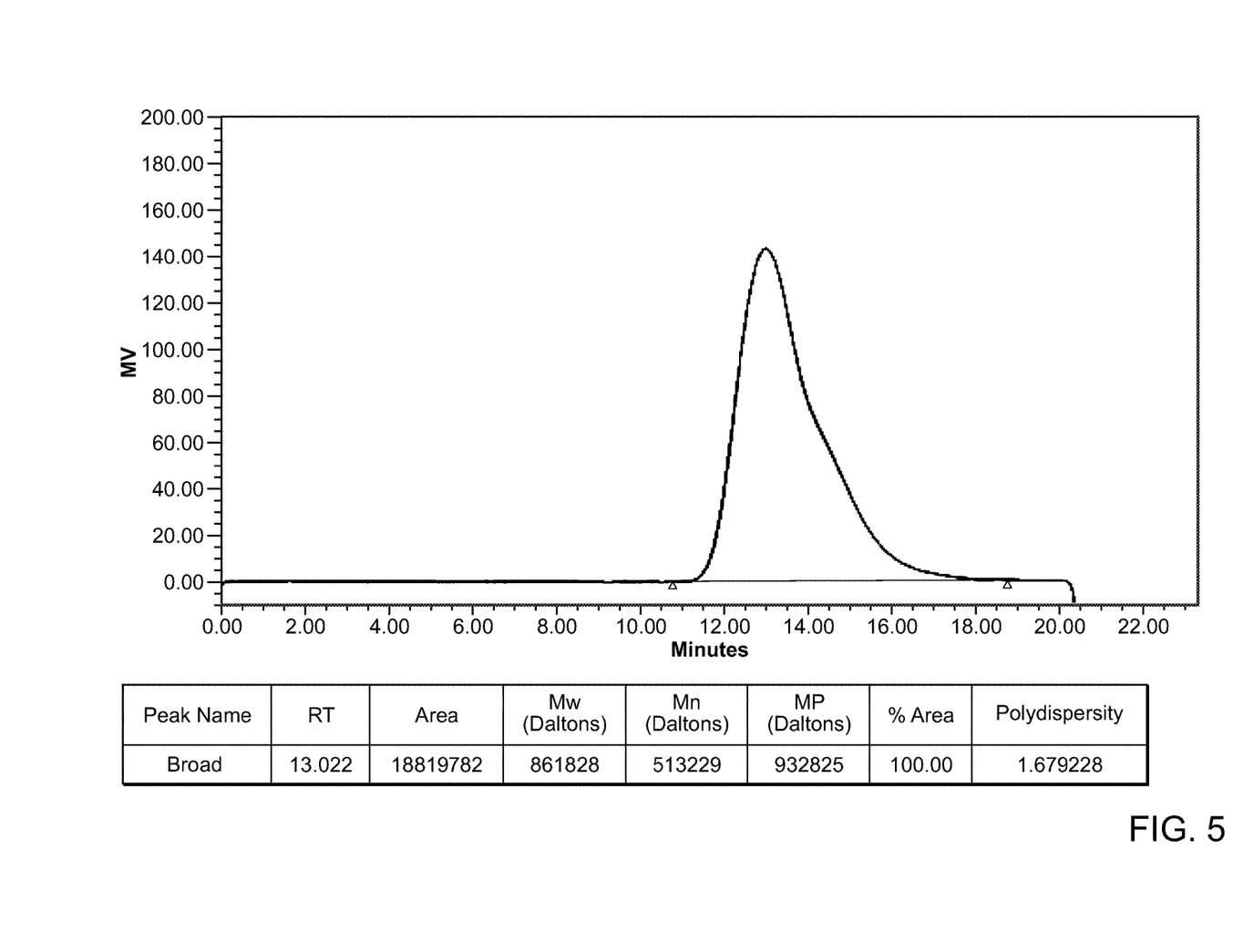
FIG. 5 HPLC profile of 19F PnPs after IEX (final PnPs/example 1)
Figure 6:
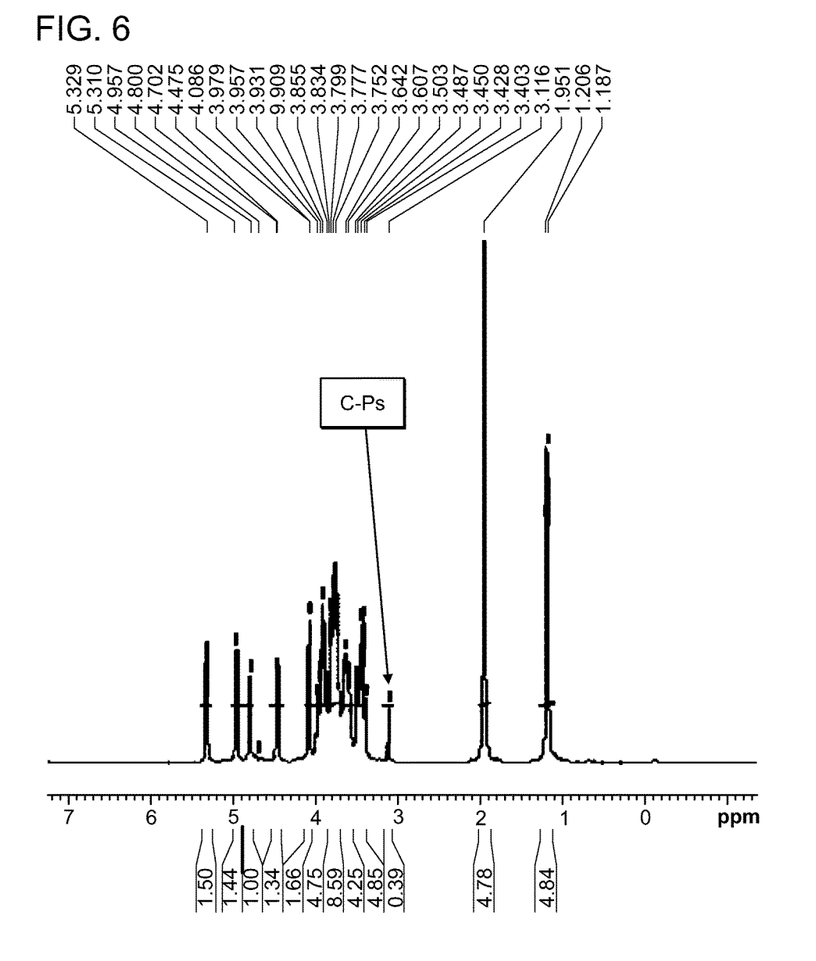
FIG. 6 NMR of 19F PnPs after IEX
Figure 7:
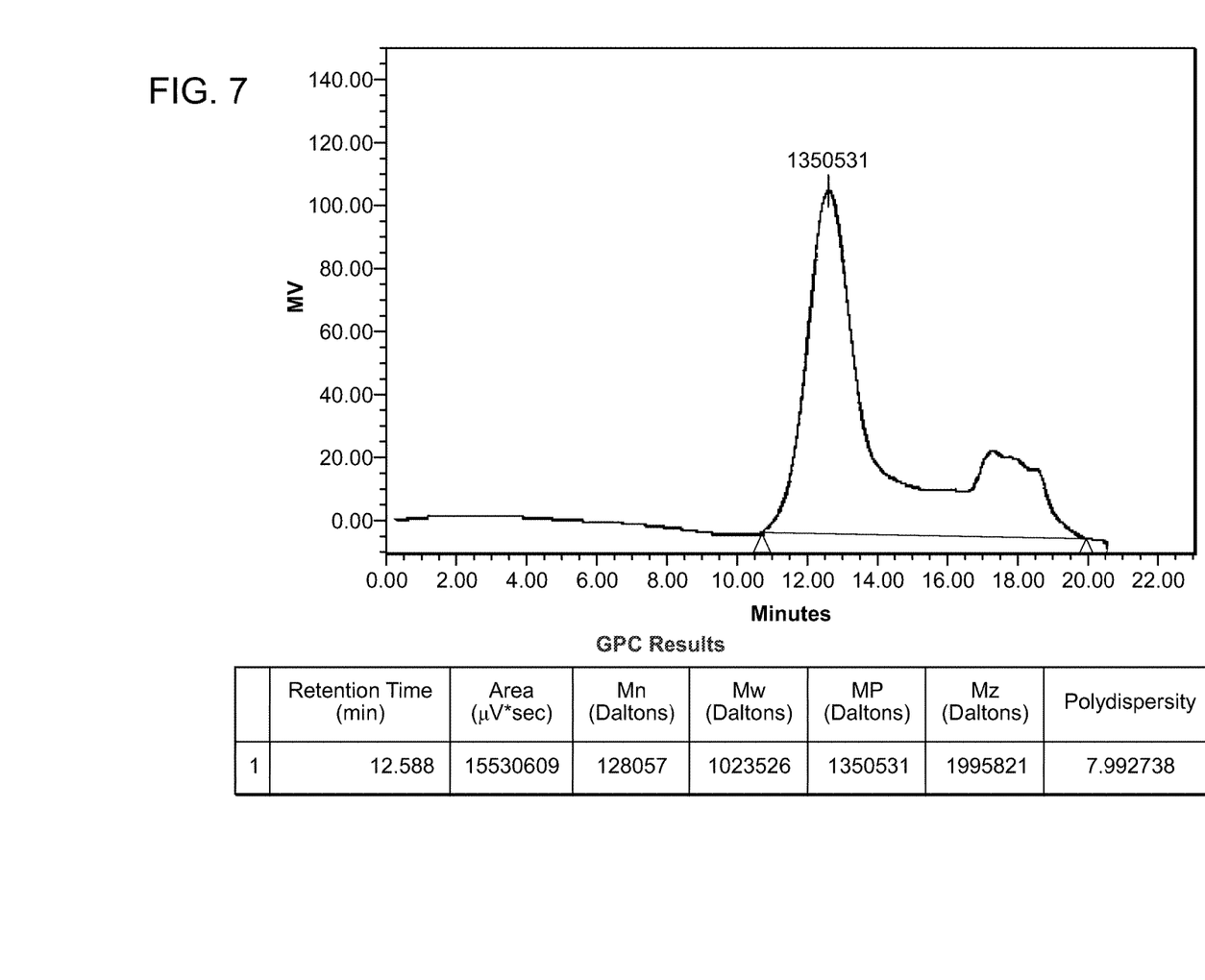
FIG. 7 Pneumococcal polysaccharide 19F-HPLC profile of pre-IEX
Figure 8:
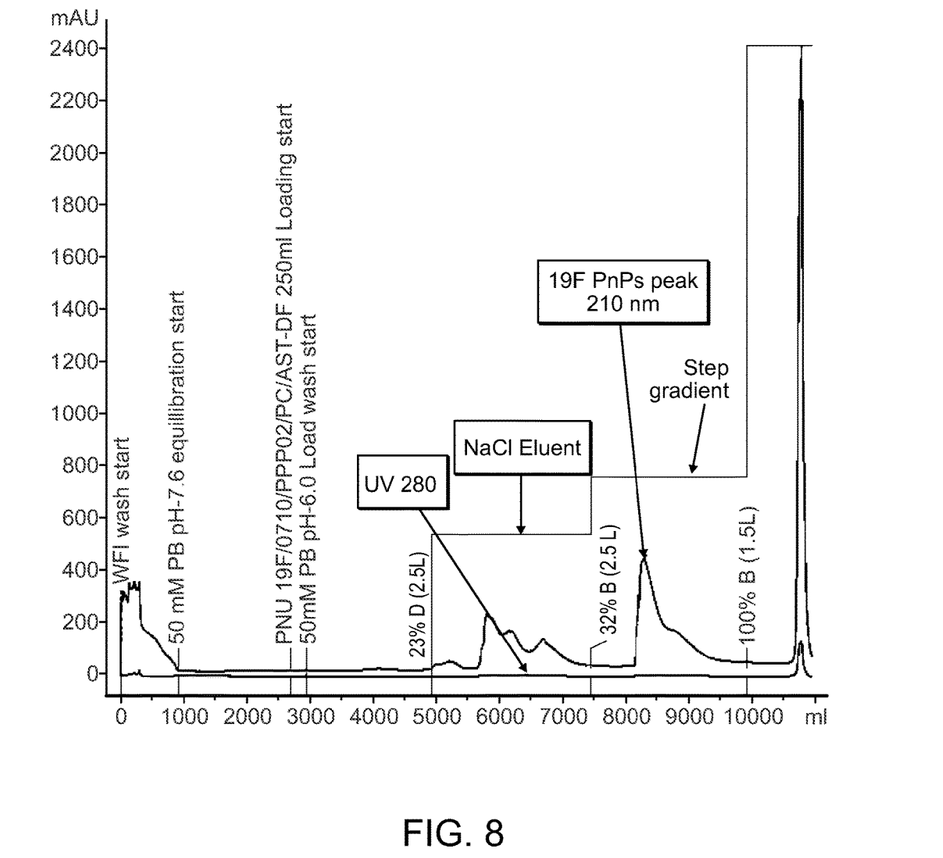
FIG. 8: Ion exchange chromatogram of pre-HIC (partially purified PnPs)
Figure 9:
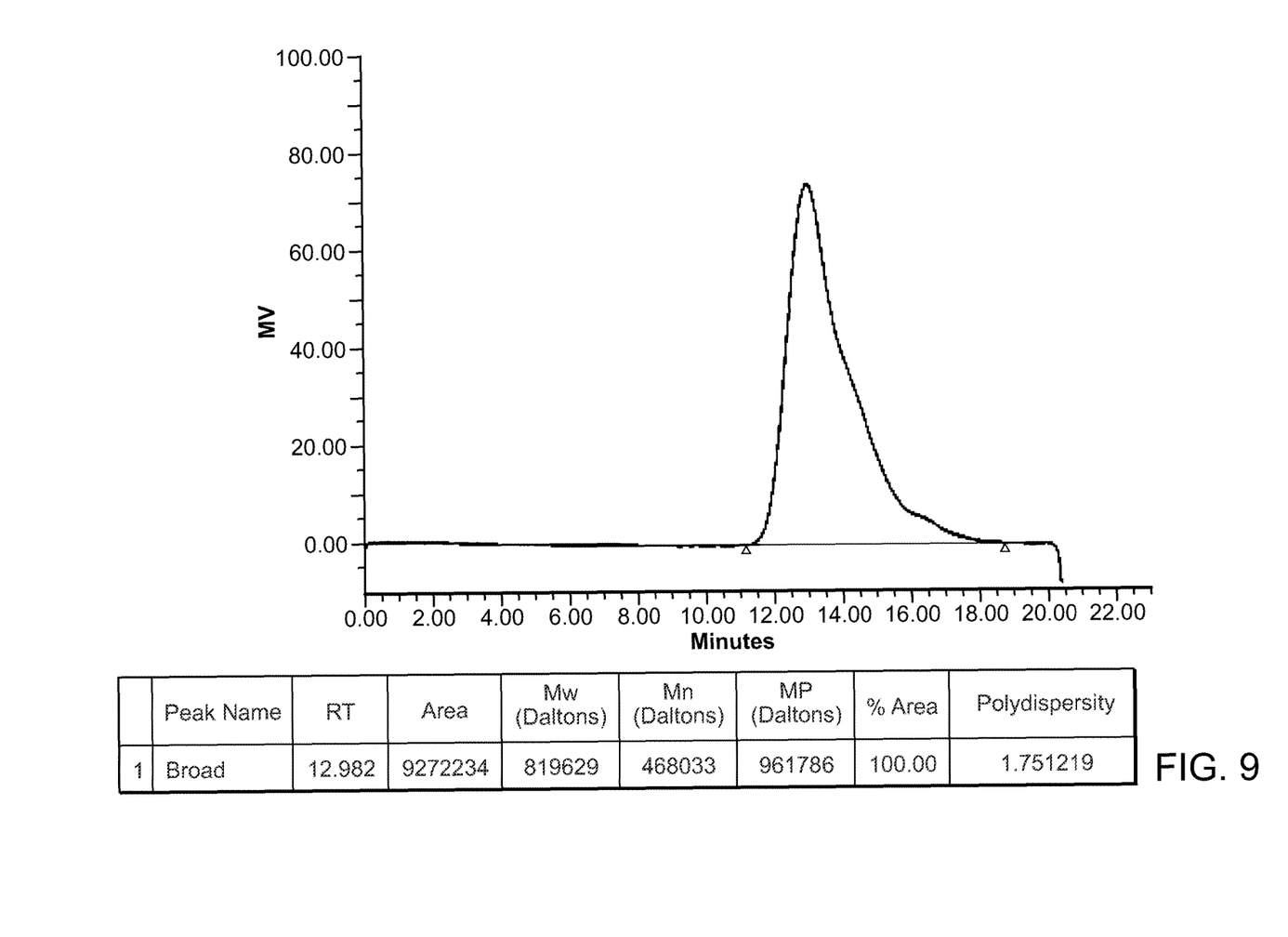
FIG. 9: HPLC profile of 19F PnPs after IEX
Figure 10:
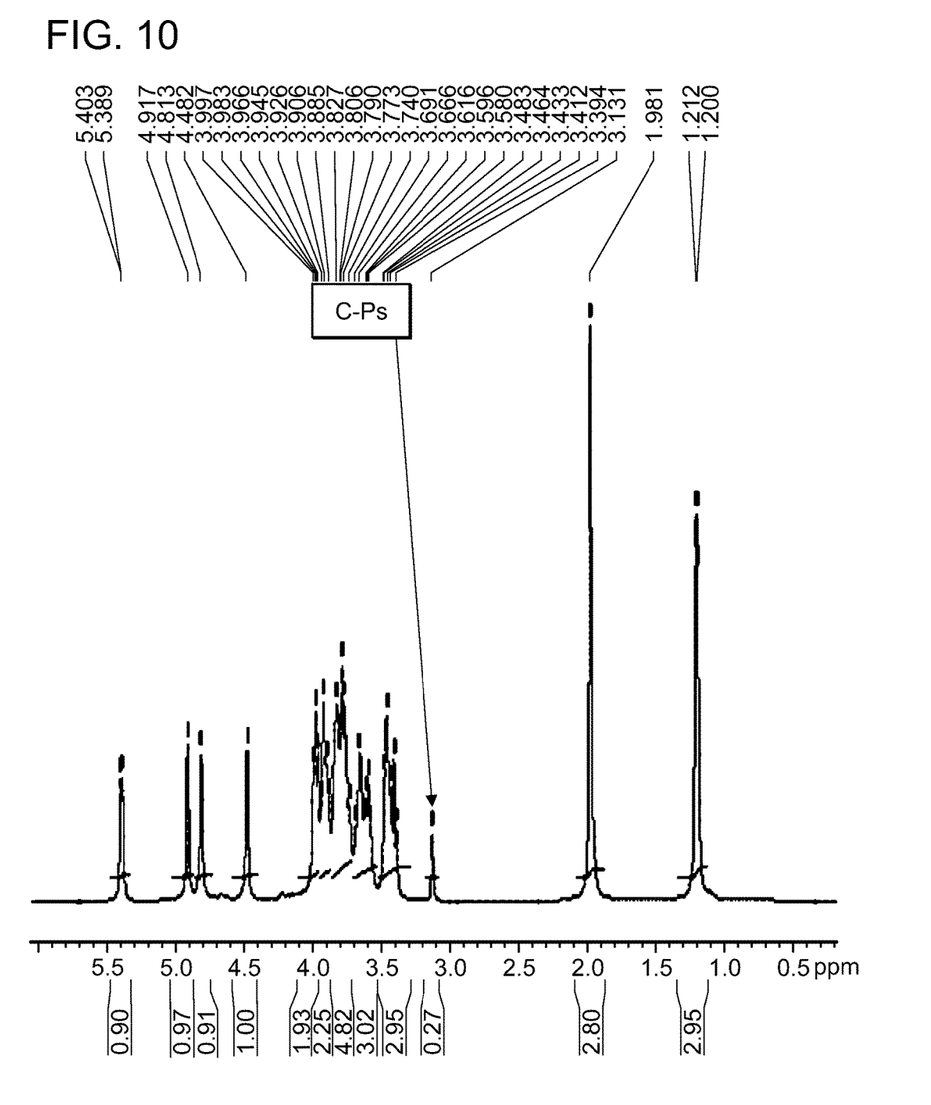
FIG. 10: NMR of 19F PnPs after IEX
Figure 11:
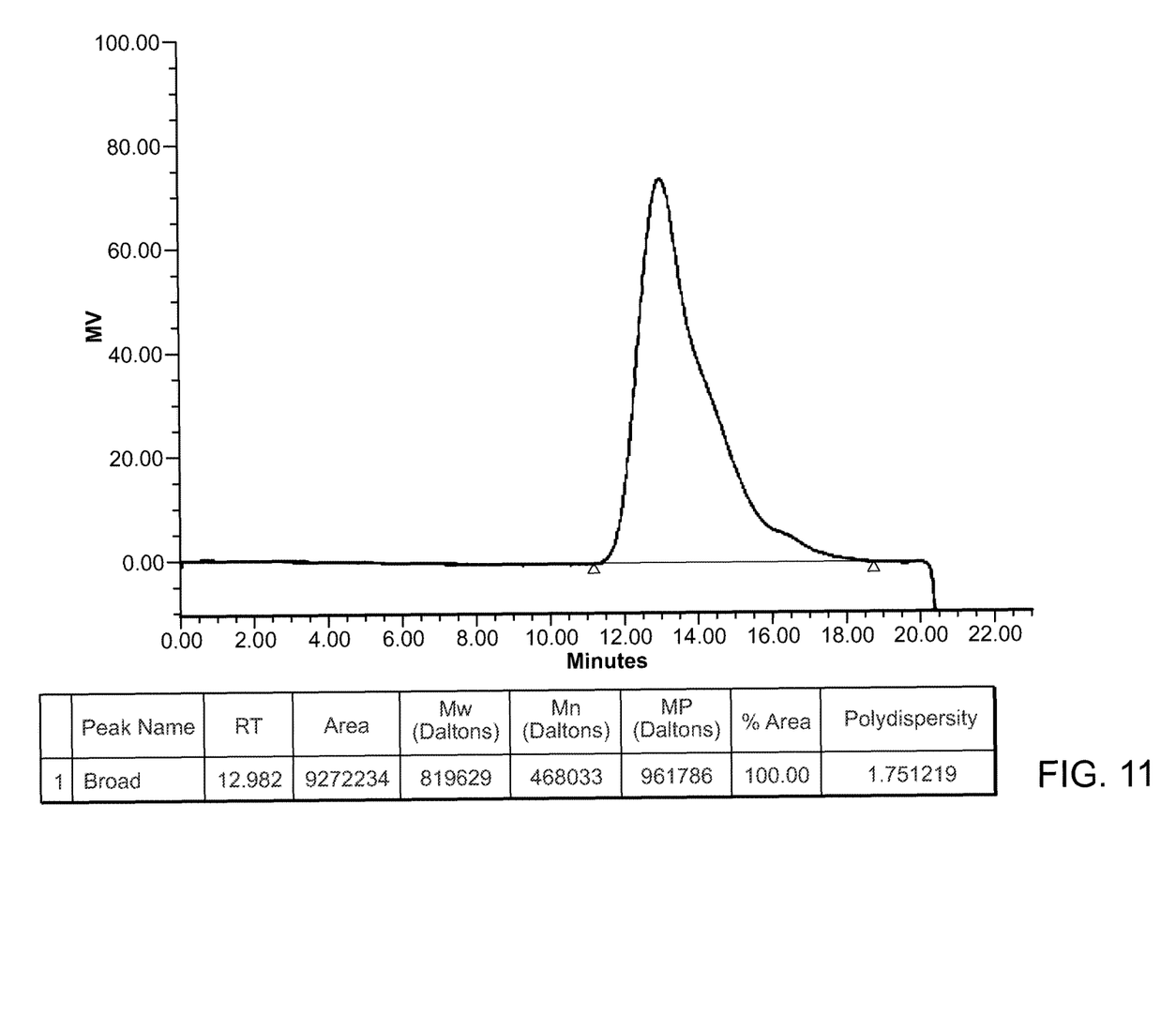
FIG. 11: HPLC profile of 19F PnPs after IEX
Figure 12:
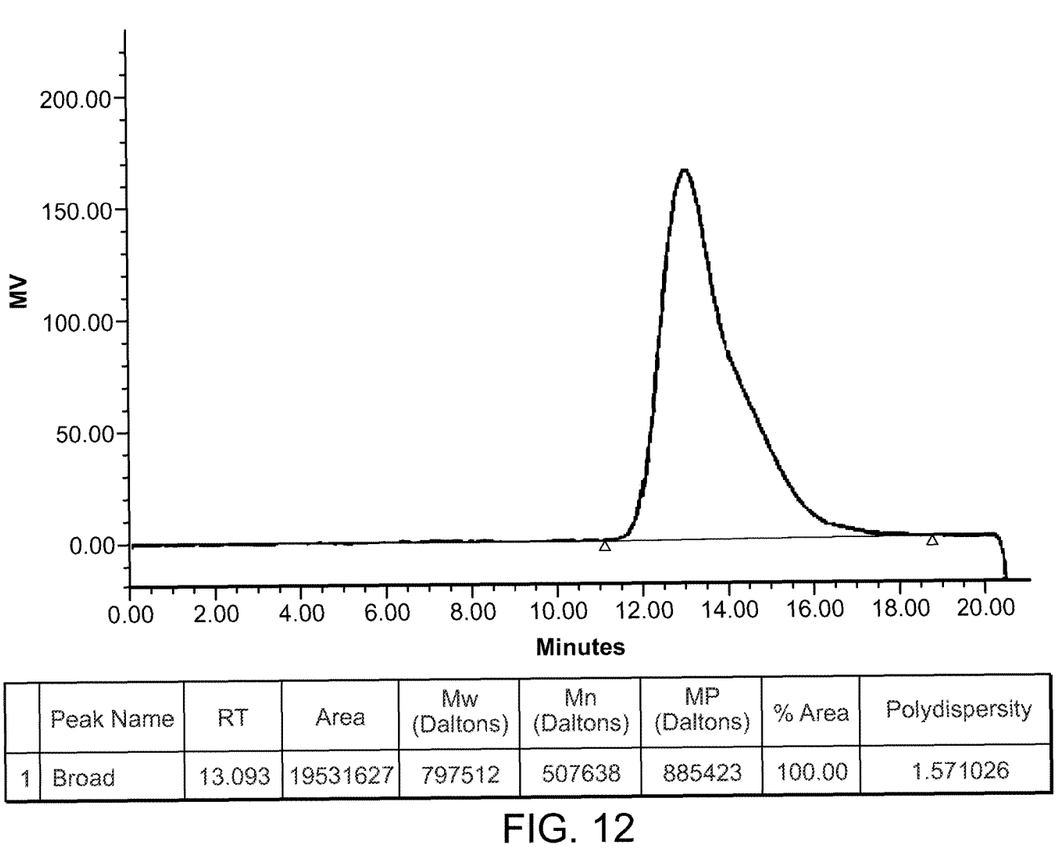
FIG. 12: HPLC profile of 19F PnPs after HIC
Figure 13:
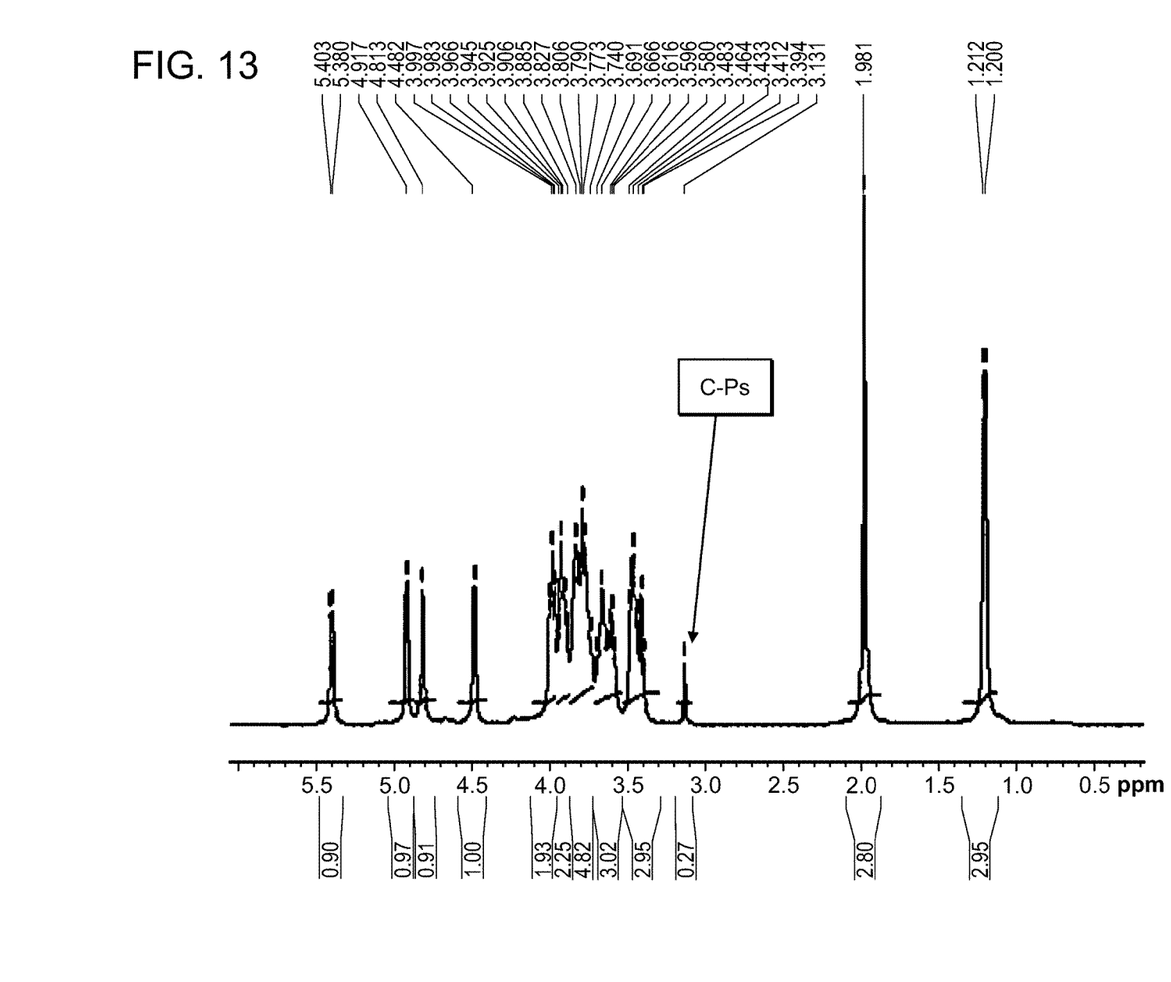
FIG. 13: NMR of 19F PnPs after IEX-HIC

In a preferred embodiment of this invention, although capsular polysaccharide is, to a large extent, purified with respect to C-Polysaccharide by using a single ion-exchange chromatography step, but a combination of hydrophobic column with ion exchange column ensures removal of C-polysaccharide as well as other contaminants like proteins and this combination improves the quality of polysaccharide like more homogeneity or less heterogeneity or low polydispersity (FIG. 4).

Preferred example of gram-positive bacteria for use according to this invention are Streptococci.

The capsular polysaccharide purified by the instant method can be derived from any of the serotypes of *Streptococcus pneumoniae* selected from: 1, 2, 3, 4, 6A, 6B, 7F, 8, 9N, 9V, 10A, 11A, 12F, 14, 15B, 17F, 18C, 19F, 19A, 20, 22F, 23F, and 33F.

A simple and novel method involving a combination of hydrophobic interaction chromatography and ion exchange steps or direct ion exchange has been developed for obtaining highly purified capsular polysaccharide.

Another embodiment of the instant invention is that PnPs prepared by the instant process can have recovery of about 60 to 70%, wherein C-polysaccharide contamination reduction can be from 1 to 5 fold as compared to C-Ps content of post-HIC or pre-ion exchange chromatography C-polysaccharide, protein contamination can be less than 1% and nucleic acid contamination can be less than 1%.

Yet another embodiment of the instant invention is that the instant purification method of C-Ps removal is very cost effective as only around 400 INR is required per liter of crude concentrate processing as against 5000 INR required for alcohol/CTAB process. The instant chromatography based method requires 80-90% less time, 90% less cost and minimum manual errors when compared with CTAB/Alcohol based methods.

Another embodiment of the instant invention is that combination of Ion exchange chromatography and Hydrophobic interaction chromatography is the preferred method for substantial reduction of C-polysaccharide and other contaminants. Alternatively use of a single step ion exchange chromatography can result in C-polysaccharide reduction to the same extent of HIC-IEX combination, complying to the IP/EP/BP/WHO limits, though other contaminants (e.g., protein, nucleic acids) are more.

EXAMPLES

Example 1

*S. Pneumoniae* Capsular Polysaccharide Serotype 19F (HIC followed by IEX)

5 L clarified broth from the fermenter cultures of *S. pneumoniae* serotype 19F was concentrated and diafiltered to 500 ml using a 100 kDa MWCO membrane. Diafiltration was accomplished using 25 mM sodium phosphate buffer at neutral pH followed by diafiltration with water for injection (WFI).

Nuclease was added to the polysaccharide solution to achieve a final concentration of 8 U/ml of solution. The enzyme treatment was carried out at 37° C., for 10±2 hrs with stirring.

Ammonium sulphate was added to the nuclease treated polysaccharide solution to 50% saturation and incubated at 2-8° C. for 12±2 hrs (except serotypes 5 and 4). The mixture was subjected to centrifugation. The pellet (precipitate) was discarded. The solution (~500 ml) is subjected to 100 kD diafiltration using NaCl followed by chilled WFI. This diafiltered solution containing polysaccharide with a buffer and high salt concentration was loaded on HIC column.

The hydrophobic interaction chromatography column (300 ml) was equilibrated with 50% saturated ammonium sulphate buffer and the polysaccharide solution (500 ml) was then loaded onto the column in pH range 6 to 8, preferably at pH 6 to 7 pH. The column was further washed with the buffer containing 50% saturated ammonium sulphate. Under these conditions, the polysaccharide was recovered in the flow-through and equilibration wash from the column.

The polysaccharide solution was then concentrated using a 100 kDa MWCO filter and then diafiltered with NaCl and Water for Injection (WFI).

The ion exchange chromatography column (300 ml) (strong anion exchanger) was equilibrated with 20 mM sodium phosphate buffer and the polysaccharide solution (500 ml) was then loaded onto the column in pH range 6 to 8, preferably at pH 6.5 to 7.5 pH. The column was further washed with buffer. The adsorbed polysaccharides were eluted with step gradient elution using 1.0 M NaCl (various polysaccharides were eluted at different ionic strengths of NaCl).

The polysaccharide solution was then concentrated using a 100 kDa MWCO filter and then diafiltered with Water for Injection (WFI).

The diafiltered polysaccharide solution was filtered through a 0.22μ membrane filter into polypropylene bottles. The purified polysaccharide was stored frozen at −20±5° C.

The above process was also utilized for serotypes 4, 6A, 6B, 7F, 9V, 10A, 14, 18C, 19A, 19F, 23F Results:—

C-Polysaccharide post HIC & post Ion exchange chromatography was estimated by $H^1/P^{31}$ NMR spectra (Refer table 1)

TABLE 1

Residual C-Ps of pre-(after HIC) and post-IEX

| Pneumococcal Serotypes | Existing C-Ps amount after HIC(pre-ion exchange) | | C-Ps after Ion exchange chromatograpy(IEX) | | |
|---|---|---|---|---|---|
| | Wt % | Mole % | Wt % | Mole % | Fold reduction |
| 6B | 7 | 3.727 | 2.73 | 1.45 | 2.5 |
| 9V | 12.51 | 8.797 | 5.008 | 3.522 | 2.5 |
| 14 | 14.1 | 8.56 | 5.17 | 3.136 | 2.7 |
| 19A | 9.2 | 4.264 | 2.91 | 1.34 | 3.2 |
| 19F | 10.3 | 4.764 | 3.17 | 1.47 | 3.2 |
| 23F | 10.6 | 6.345 | 5.8 | 3.47 | 1.8 |
| 6A | 7.04 | 3.34 | 1.39 | 0.74 | 5 |
| 4 | 30 | 15.97 | 12.03 | 6.38 | 2.5 |
| 18C | 12.3 | 6.54 | 3.6 | 1.91 | 3.5 |
| 7F | 14.4 | 7.66 | 7.36 | 3.90 | 1.9 |

Example 2

*S. Pneumoniae* Capsular Polysaccharide Serotype 19F (Direct IEX)

Clarified broth 5 L from the fermenter cultures of *S. pneumoniae* serotype 19F was concentrated and diafiltered to ~500 ml using a 100 kDa MWCO membrane. Diafiltration was accomplished using 25 mM sodium phosphate buffer at neutral pH followed by diafiltration by water for injection (WFI).

Nuclease was added to the polysaccharide solution to achieve a final concentration of 8 U/ml of solution. The enzyme treatment was carried out at 37° C., for 10±2 hrs.

Ammonium sulphate was added to the nuclease-treated polysaccharide solution to 50% saturation and incubated at 2-8° C. for 12±2 hrs. The mixture was subjected to centrifugation. The pellet (precipitate) was discarded. The solution (~500 ml) containing polysaccharide was diafiltered against 20 mM Tris HCl, 2 mM MgCl2 pH 8.0±0.2, using 100 kDa MWCO membrane.

The polysaccharide solution was then further diafiltered against Water for Injection (WFI) using a 100 kDa MWCO filter till constant conductivity was achieved.

The ion exchange chromatography column (300 ml) (strong anion exchanger) was equilibrated with 20 mM sodium phosphate buffer and the polysaccharide solution (500 ml) was then loaded onto the column in pH range 6 to 8, preferably at pH 6.5 to 7.5 pH. The column was further washed with buffer. The adsorbed polysaccharides were eluted with step gradient elution using 1.0 M NaCl (various polysaccharides were eluted at different ionic strengths of NaCl).

The polysaccharide solution was then concentrated using a 100 kDa MWCO filter and then diafiltered with Water for Injection (WFI).

The diafiltered polysaccharide solution was filtered through a 0.22 g membrane filter into polypropylene bottles. The purified polysaccharide was stored frozen at −20±5° C.

The above process was also utilized for serotypes 6A, 6B, 7F, 9V, 10A, 14, 18C, 19A, 19F, 23F Results:—

C-Polysaccharidepost Ion exchange chromatography only was estimated by $H^{1}/P^{31}$ NMR spectra (Refer table 2)

TABLE 2

| Residual C-Ps after direct IEX | | |
|---|---|---|
| | C-Ps after Direct Ion exchange chromatography (IEX) | |
| Serotypes | Wt % | Mole % |
| 19A | 3.56 | 1.64 |
| 19F | 3.3 | 1.53 |
| 6A | 2.17 | 1.0 |
| 4 | 6.9 | 3.17 |
| 18C | 19 | 8.72 |
| 7F | 6.7 | 3.04 |

Example 3

S. Pneumoniae Capsular Polysaccharide Serotype 19F (IEX followed by HIC)

Clarified broth 5 L from the fermenter cultures of S. pneumoniae serotype 19F was concentrated and diafiltered to ~500 ml and using a 100 kDa MWCO membrane. Diafiltration was accomplished using 25 mM sodium phosphate buffer at neutral pH followed by diafiltration by water for injection (WFI).

Nuclease was added to the polysaccharide solution to achieve a final concentration of 8 U/ml of solution. The enzyme treatment was carried out at 37° C., for 10±2 hrs.

Ammonium sulphate was added to the nuclease-treated polysaccharide solution to 50% saturation and incubated at 2-8° C. for 12±2 hrs. The mixture was subjected to centrifugation. The pellet (precipitate) was discarded. The solution (500 ml) containing polysaccharide was diafiltered against 20 mM Tris HCl, 2 mM MgCl2 pH 8.0±0.2, using 100 kDa MWCO membrane.

The polysaccharide solution was then further diafiltered against Water for Injection (WFI) using a 100 kDa MWCO filter till constant conductivity was achieved.

The ion exchange chromatography column (300 ml) (strong anion exchanger) was equilibrated with 20 mM sodium phosphate buffer and the polysaccharide solution (500 ml) was then loaded onto the column in pH range 6 to 8, preferably at pH 6.5 to 7.5 pH. The column was further washed with buffer. The adsorbed polysaccharides were eluted with step gradient elution using 1.0 M NaCl (various polysaccharides were eluted at different ionic strengths of NaCl).

The hydrophobic interaction chromatography column (300 ml) was equilibrated with 50% saturated ammonium sulphate buffer and the polysaccharide solution (500 ml) from ion exchange elute was then loaded onto the column in pH range 6 to 8, preferably at pH 6 to 7 pH. The column was further washed with the buffer containing 50% saturated ammonium sulphate. Under these conditions, the polysaccharide was recovered in the flow-through and wash from the column.

The polysaccharide solution was then concentrated and diafiltered against NaCl followed by Water for Injection (WFI) using a 100 kDa MWCO filter.

The diafiltered polysaccharide solution was filtered through a 0.22µ membrane filter into polypropylene bottles. The purified polysaccharide was stored frozen at −20±5° C.

The above process was also utilized for serotypes 6A, 6B, 7F, 9V, 10A, 14, 18C, 19A, 23F Results:—

C-Polysaccharide post Ion exchange chromatography & post hydrophobic interaction chromatography was estimated by $H^{1}/P^{31}$ NMR spectra (Refer table 3)

TABLE 3

| | C-Ps after Ion exchange chromatography (IEX) | | C-Ps after Hydrophobic interaction chromatography (HIC) | |
|---|---|---|---|---|
| Serotypes | Wt % | Mole % | Wt % | Mole % |
| 19A | 3.56 | 1.64 | 3.39 | 1.56 |
| 19F | 3.3 | 1.53 | 3.04 | 1.41 |
| 6A | 2.17 | 1.0 | 2.39 | 1.1 |
| 4 | 6.9 | 3.17 | 6.20 | 2.85 |
| 18C | 19 | 8.72 | 17.2 | 7.89 |
| 7F | 6.7 | 3.04 | 6.9 | 3.13 |

Example 4

S. Pneumoniae Capsular Polysaccharide Serotype 4

Clarified broth 5 L from the fermenter cultures of S. pneumoniae serotype 4 was concentrated and diafiltered to ~500 ml and using a 100 kDa MWCO membrane. Diafiltration was accomplished using 25 mM sodium phosphate buffer at neutral pH followed by diafiltration by water for injection (WFI).

Enzyme was added to the polysaccharide solution to achieve a final concentration of 10 U/ml of solution. The enzyme treatment was carried out at 37° C., for 10±2 hrs.

Sodium deoxycholate (0.5% w/v) and NaCl (60 mM) was added to the enzyme-treated polysaccharide solution to and incubated at 2-6° C. for 10±2 hrs. The mixture was subjected to centrifugation. The pellet (precipitate) was discarded. The solution (~400 ml) containing polysaccharide was diafiltered against 20 mM Tris HCl, 2 mM MgCl2 pH 8.0±0.2, using 100 kDa MWCO membrane.

The polysaccharide solution was then further diafiltered against Water for Injection (WFI) using a 100 kDa MWCO filter till constant conductivity was achieved.

Polysaccharide was chromatographically purified as per the techniques illustrated in examples 1 or 2 or 3.

The diafiltered polysaccharide solution was filtered through a 0.22μ membrane filter into polypropylene bottles. The purified polysaccharide was stored frozen at −20±5° C.

The above process was also utilized for serotype 4

TABLE 4

| Serotypes | Scale | % Recovery of Polysaccharide | % Protein | % Nucleic Acid | % C-Ps | % Reduction of C-Ps |
|---|---|---|---|---|---|---|
| 19F | R & D scale | 70 | 0.69 | 0.03 | 3.09 | 69.22 |
| 19F | Pilot scale | 66 | 0.80 | 0.60 | 3.29 | 65.48 |
| 19F | Manufacturing Scale | 65 | 0.42 | 0.20 | 3.17 | 63.57 |

The results indicate that polysaccharide recovery of about 60 to 70% is obtained, C-polysaccharide contamination reduction is of 1 to 5 fold as compared to the C-Ps content of post-HIC or pre ion exchange chromatography, protein contamination is less than 1% and nucleic acid contamination is less than 1%, wherein 80-90% less time is consumed & 90% less cost incurred when compared with CTAB/Alcohol based prior art methods.

Hydrophobic interaction chromatography followed by Ion exchange chromatography is the preferred method for substantial reduction of C-polysaccharide and other contaminants. The process wherein the sequence of chromatography is reversed (i.e. Ion exchange followed by Hydrophobic interaction) also results in substantial C-Polysaccharide removal. Alternatively use of single step ion exchange chromatography can result in C-polysaccharide reduction and other contaminants (e.g. protein, nucleic acids) compliant with standard specifications of final polysaccharide.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are/therefore intended to be embraced therein.

We claim:

1. A cost effective, alcohol- & cetyltrimethylammonium bromide (CTAB)-free chromatography based method for removal of C-polysaccharide from an antigenic polysaccharide which comprises:
   (a) lysing bacterial cells in a fermentation medium with deoxycholate thereby producing an aqueous cell lysate containing a polysaccharide solution and solid cell debris;
   (b) clarifying the aqueous cell lysate by separating the solid cell debris from the polysaccharide solution;
   (c) concentrating the polysaccharide solution by ultrafiltration using a 100 kDa molecular weight cutoff membrane to remove low molecular weight contaminants and to form a solution of concentrated polysaccharide;
   (d) treatment of the solution of concentrated polysaccharide with a nuclease;
   (e) precipitation of impurities from the solution of concentrated polysaccharide using ammonium sulphate or sodium deoxycholate treatment;
   (f) diafiltration of the solution of concentrated polysaccharide using a 100 kDa molecular weight cutoff membrane;
   (g) subjecting the solution of concentrated polysaccharide to a multi-step chromatography to produce a purified polysaccharide solution, wherein the multi-step chromatography comprises hydrophobic interaction chromatography (HIC) followed by ion exchange chromatography (IEX);
   (h) concentration and diafiltration of the purified polysaccharide solution; and
   (i) sterile filtration of the purified polysaccharide solution;
      wherein the purified polysaccharide solution shows a 1- to 5-fold reduction of type-specific C-polysaccharide contamination relative to a purified polysaccharide solution obtained by subjecting the solution of concentrated polysaccharide to a single step HIC or ion exchange chromatography; and
      wherein the antigenic polysaccharide is a polysaccharide from *S. pneumoniae* serotype 18C.

2. The method according to claim 1, wherein the purified polysaccharide solution shows protein contamination less than 1% and nucleic acid contamination less than 1%.

3. The method according to claim 1, wherein the method requires at least 80% less time and at least 90% less cost than CTAB/Alcohol based methods.

4. The method according to claim 1, wherein the hydrophobic interaction chromatography support is selected from the group consisting of butyl-agarose, phenyl-agarose, octyl-agarose, phenyl-sepharose and organic polymer resin functionalized with a group selected from butyl, phenyl or ether.

5. The method according to claim 1, wherein the hydrophobic interaction chromatography column is run in the pH range of 5 to 8.

6. The method according to claim 1, wherein the hydrophobic interaction chromatography uses a buffer of sodium or potassium phosphate containing 2 M to 5 M sodium chloride salt.

7. The method according to claim 1, wherein the ion exchange chromatography is an anion exchange chromatography.

8. The method according to claim 7, wherein the anion exchange chromatography is performed on an anion exchange resin selected from the group consisting of DEAE cellulose, MonoQ, Capto Q, Eshmino Q, Gigacap Q 650M, Nuvia-Q, Cellufine Q-h, MiniQ, Source 15Q and 30Q, Q, DEAE Sepharose Fast Flow, Q Sepharose high Performance, QAE SEPHADEX™ and FAST Q SEPHAROSE™ (GE Healthcare), UNOsphere Q, Macro-Prep DEAE and Macro-Prep High Q from Biorad, Ceramic HyperD Q, ceramic HyperD DEAE, Toyopearl SuperQ-650S, 650M and 650C, QAE-550C and 650S, DEAE-650M.

9. The method according to claim 8, wherein the anion exchange chromatography is performed on an anion exchange resin Gigacap Q 650M.

10. The method according to claim 7, wherein the anion exchange column is eluted at 10 to 60% of 1 M NaCl in phosphate buffer.

11. The method according to claim 10, wherein the anion exchange column is eluted at any one or more of 10%, 15%, 20%, 25%, 30%, 45% and 60% of 1 M NaCl in phosphate buffer.

12. The method according to claim 11, wherein the anion exchange column is eluted at a linear or step gradient of 1 M NaCl in phosphate buffer.

13. The method according to claim 10, wherein the anion exchange column is carried out using phosphate buffer ranging from 10 mM to 300 mM.

14. The method according to claim 7, wherein the anion exchange chromatography is run in the pH range of 5 to 8.

* * * * *